(12) United States Patent
Huang et al.

(10) Patent No.: US 12,391,032 B2
(45) Date of Patent: Aug. 19, 2025

(54) DICING AND PARTIAL DICING RELEASE OF LITHOGRAPHED DEVICE

(71) Applicant: Neuralink Corp., Fremont, CA (US)

(72) Inventors: Yu Niu Huang, Fremont, CA (US); Peter J. Gilgunn, Fremont, CA (US); Dominic A. Herincx, Fremont, CA (US); Zachary M. Tedoff, Fremont, CA (US)

(73) Assignee: Neuralink Corp., Fremont, CA (US)

( * ) Notice: Subject to any disclaimer, the term of this patent is extended or adjusted under 35 U.S.C. 154(b) by 456 days.

(21) Appl. No.: 17/828,428

(22) Filed: May 31, 2022

(65) Prior Publication Data

US 2023/0382098 A1    Nov. 30, 2023

(51) Int. Cl.
*B32B 38/00* (2006.01)
*A61N 1/05* (2006.01)
*B32B 27/28* (2006.01)

(52) U.S. Cl.
CPC ........ *B32B 38/0004* (2013.01); *A61N 1/0529* (2013.01); *B32B 27/281* (2013.01); *B32B 2535/00* (2013.01)

(58) Field of Classification Search
CPC .............. B32B 38/0004; B32B 27/281; B32B 2535/00; A61N 1/0529
See application file for complete search history.

(56) References Cited

U.S. PATENT DOCUMENTS

| | | | |
|---|---|---|---|
| 8,312,626 B2 * | 11/2012 | Suzuki | G01R 3/00 |
| | | | 29/874 |
| 11,107,703 B2 | 8/2021 | Tolosa et al. | |
| 11,444,056 B2 | 9/2022 | Chen et al. | |
| 2013/0131485 A1 * | 5/2013 | Oh | A61B 5/24 |
| | | | 29/829 |
| 2018/0296243 A1 | 10/2018 | Hanson et al. | |
| 2020/0086111 A1 | 3/2020 | Young et al. | |

* cited by examiner

*Primary Examiner* — George R Koch
*Assistant Examiner* — Christopher C Caillouet
(74) *Attorney, Agent, or Firm* — Oblon, McClelland, Maier & Neustadt, L.L.P.

(57) ABSTRACT

The disclosure provides a method for fabricating a cantilever section in a structure, which includes providing a structure comprising a substrate, a compliant layer and a sacrificial layer therebetween; cutting part-way through the substrate to create an at least one linear partial cut; releasing the sacrificial layer from the structure; and breaking the substrate along the at least one linear partial cut to generate a cantilever section in a substrate.

20 Claims, 7 Drawing Sheets

DICING AND PARTIAL DICING RELEASE OF LITHOGRAPHED DEVICE

BACKGROUND

US 2018/0296243 to Hanson teaches methods and systems for implanting an implantable device into a mammalian brain. The implantable device includes: (i) a biocompatible substrate, (ii) a conduit (e.g., an electrode, a waveguide) that is disposed on the biocompatible substrate, and (iii) an engagement feature (e.g., a loop) for reversible engagement with an insertion needle. The biocompatible substrate can be flexible. The implantable device is implanted using an insertion needle that includes an engagement feature corresponding to the engagement feature of the implantable device. To implant, an implantable device is reversibly engaged with an insertion needle, the device-loaded insertion needle is inserted into a biological tissue (e.g., to a desired depth), and the insertion needle is retracted, thereby disengaging the implantable device from the insertion needle and allowing the implantable device to remain implanted in the brain.

US 2020/0086111 to Young teaches a system and method for implanting devices into biological tissue (e.g., brain tissue). The system can include a biocompatible probe, an integrated circuit (IC) chip tethered to the probe, a cartridge comprising a temporary attachment surface by which the probe is removably coupled to the cartridge and a fastener for removably coupling the IC chip to the cartridge, a needle to reversibly engage with the probe, a robotic arm to hold the needle, a camera, and a microprocessor controller. The microprocessor controller can control the robotic arm and the needle to remove the probe from the temporary attachment surface using the needle, pierce the biological tissue with the needle and the probe, withdraw the needle while leaving the probe within the biological tissue; and detach the IC chip from the cartridge, leaving the IC chip with the biological tissue, with the IC chip still tethered to the probe.

In view of the foregoing, there is a need to facilitate removal of neural electrodes from a substrate prior to piercing biological tissue. The present disclosure satisfies this need and offers other advantages as well.

BRIEF SUMMARY

The present disclosure provides a structure with a cantilever and methods for fabricating the structure using partial dicing. As such, in one embodiment, the present disclosure provides a method for fabricating a cantilever section in a structure, the method comprising:
  providing a structure comprising a substrate, a compliant layer and an optional sacrificial layer therebetween;
  cutting part-way through the substrate to create an at least one linear partial cut;
  undercutting into the substrate, or if present, releasing the sacrificial layer from the structure; and
  breaking the substrate along the at least one linear partial cut to generate a cantilever section in a substrate.

In certain aspects, the substrate is a member selected from a wafer, plate or film.

In certain aspects, the substrate comprises silicon, such as a silicon wafer.

In certain aspects, the compliant layer comprises a device.

In certain aspects, the device is implantable into a mammal such as a human. The device can be a neural electrode.

In certain aspects, the compliant layer is made or fabricated from a material, which is a member selected from polyimide, parylene C, SU-8 photoresist or benzocyclobutene (BCB).

In certain aspects, the sacrificial layer is a member selected from aluminum, chromium, silicon oxide, titanium or tungsten.

In certain aspects, the substrate (beneath the compliant layer) is undercut using an etchant.

In certain aspects, in the method without a sacrificial layer, the substrate will be immediately beneath the compliant layer.

In certain aspects, in the method that includes a sacrificial layer, the substrate will be immediately beneath the sacrificial layer.

In certain aspects, the sacrificial layer is removed using an etchant.

In certain aspects, breaking the substrate along the at least one linear partial cut to generate a cantilever section is performed in a solution or in air.

In certain aspects, the breaking step is performed manually or in automated fashion.

These and other aspects, objects and embodiments will become more apparent when read with the detailed description and figures that follow.

DETAILED DESCRIPTION

Embodiments

In one embodiment, the present disclosure provides a method for fabricating a cantilever section in a structure, the method comprising:
  providing a structure comprising a substrate, a compliant layer and an optional sacrificial layer therebetween;
  cutting part-way through the substrate to create an at least one linear partial cut;
  undercutting into the substrate, or if present, releasing the sacrificial layer from the structure; and
  breaking the substrate along the at least one linear partial cut to generate a cantilever section in a substrate.

Figure 1:
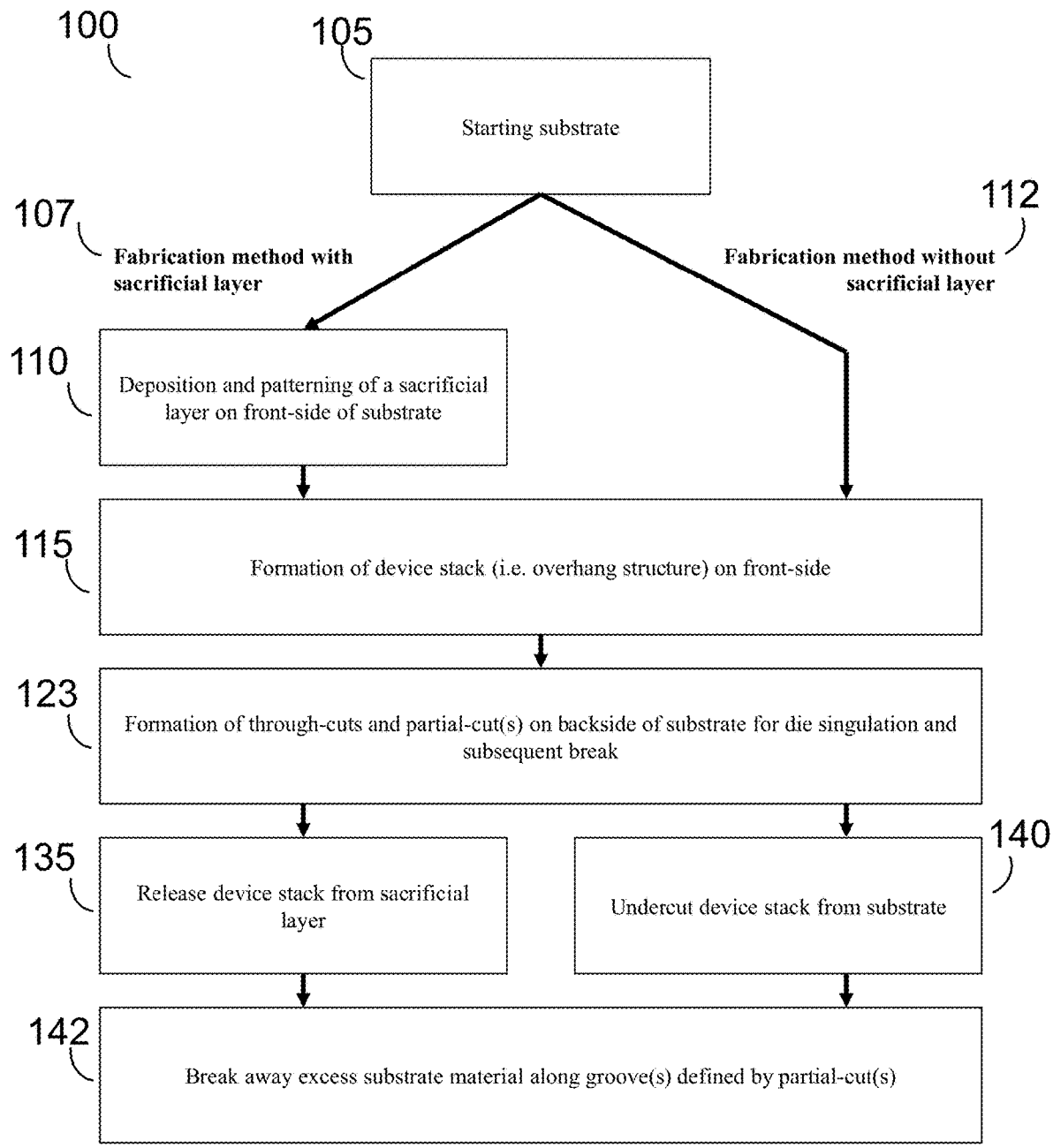
FIG. 1 illustrates a method of the present disclosure.

FIG. 1 illustrates a method 100 of the present disclosure. In certain aspects, the disclosure provides a method with an embodiment having a sacrificial layer 107, or alternatively, with an embodiment having an optional sacrificial layer i.e., the method does not include a sacrificial layer 112. Either embodiment starts with a substrate 105.

In step 110, a sacrificial layer is deposited and patterned on a first side (e.g., front side) of a substrate 105. The substrate is selected from a wafer, plate, or film. In certain aspects, the substrate comprises silicon, such as a silicon wafer.

In certain instances, the substrate or silicon wafer (e.g., die) has a dimension of about 50 mm to about 55 mm such as about 52 mm to about 53 mm (Y dimension)×about 8 mm to about 15 mm such as about 12 mm to about 13 mm (X dimension). In one aspect, the die is about 52.2 mm in the Y dimension and about 13.0 mm in the X dimension.

In certain aspects, the sacrificial layer is a member selected from aluminum, chromium, silicon oxide, titanium, or tungsten.

In step 115, embodiment 107 or embodiment 112 includes formation of a device stack (i.e., an overhang structure) on the front side.

In step 123, the method provides cutting part-way through the substrate to create an at least one linear partial cut. In other words, the method provides forming through cuts and/or partial cuts on the second side (backside) of the substrate for die singulation and subsequent break.

In step 135, the method of embodiment 107 next provides the step of releasing the device stack from the sacrificial layer. In certain instances, the sacrificial layer underneath the complaint layer (e.g. cantilever) is released by an etchant. The choice of etchant can be either a wet etchant (e.g. acid) or a dry etchant (e.g. gaseous or plasma).

In step 140, the method of embodiment 112 next provides undercutting the device stack from the substrate. In certain instances, the substrate underneath the complaint layer (e.g. cantilever) is undercut by an etchant. The choice of etchant can be either a wet etchant (e.g. acid) or a dry etchant (e.g. gaseous or plasma).

In step 142, the method 100 provides the step of breaking away excess substrate material along a groove or score defined by partial-cut(s) to provide a cantilever section in a structure. In certain aspect, this breaking step can be done manually or in an automated fashion.

In certain aspects, the disclosure provides a structure having a cantilever section made by the present methods.

Figure 2A:
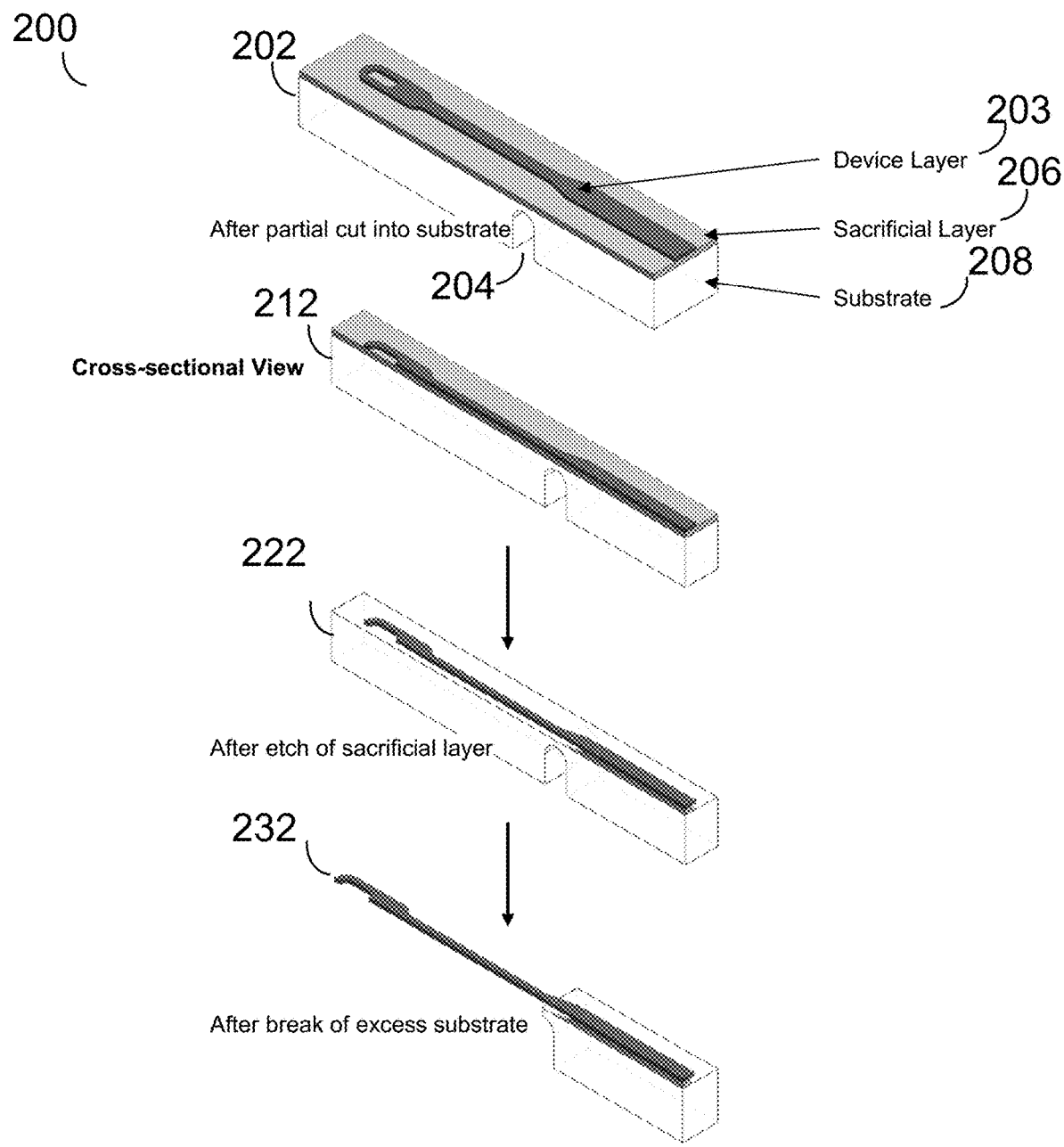
FIG. 2A shows a cross-sectional view of structures fabricated with a sacrificial layer using a method of the present disclosure.

Turning now to FIG. 2A, an embodiment of the methods of the present disclosure are shown schematically. In method 200, a structure 202 is shown having a substrate 202 with a sacrificial layer 206 disposed on the substrate 208 and a device layer 203 or compliant layer disposed on top of the sacrificial layer. Structure 202 shows a partial cut 204 into the substrate. FIG. 2A shows a cross-sectional view 212 of structure 202.

In certain aspects, as shown in FIG. 2A, the sacrificial layer is removed using an etchant such as an acid. Structure 222 shows the structure after the sacrificial layer is removed. Structure 232 shows the break-away of excess substrate. In certain aspects, the disclosure provides a structure 202, 222 and 232.

In certain aspects, the disclosure provides a substrate having a cantilever device or complaint layer disposed on top thereof.

Figure 2B:
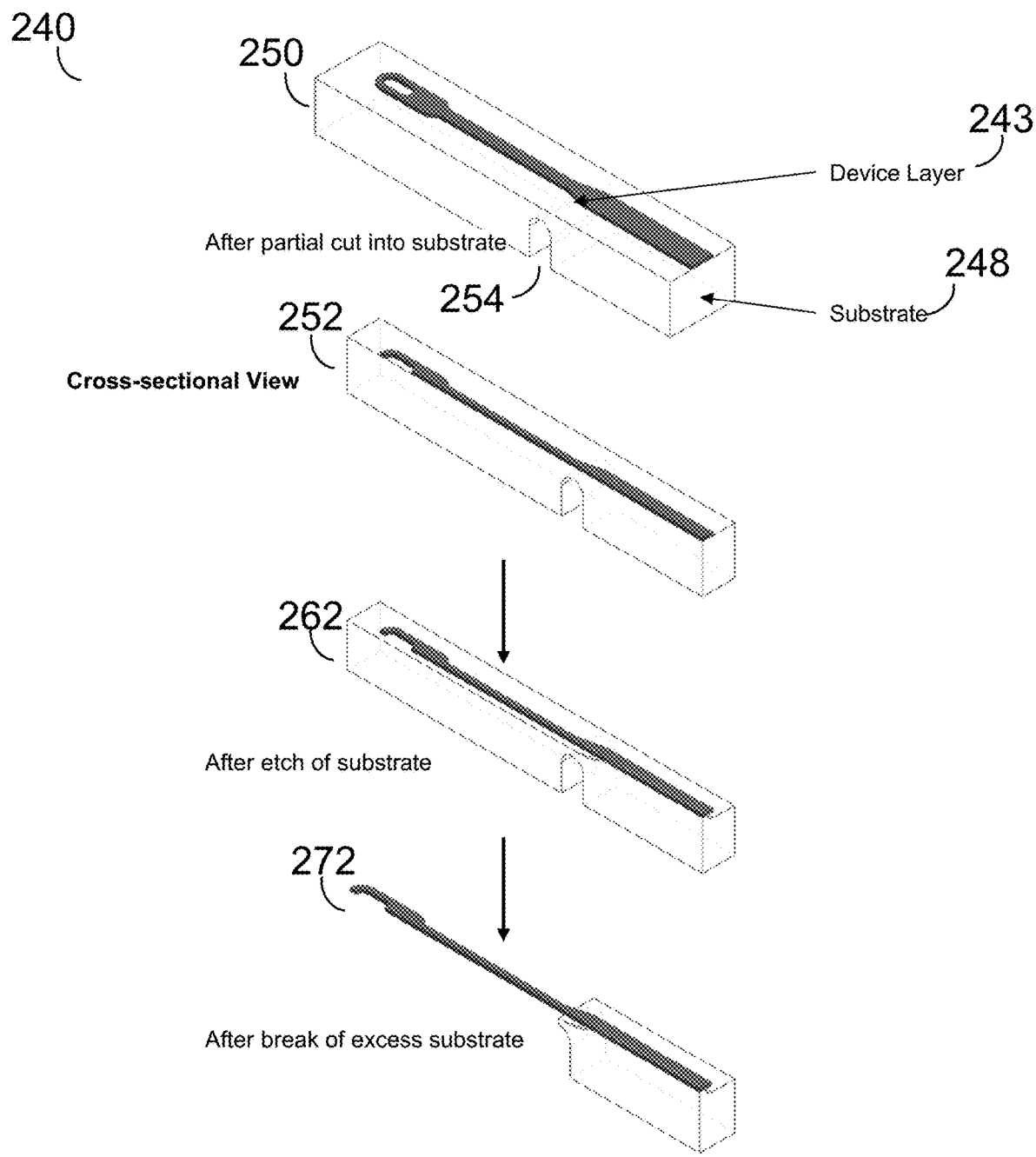
FIG. 2B shows a cross-sectional view of structures fabricated without a sacrificial layer using a method of the present disclosure.

Turning now to FIG. 2B, an embodiment of the methods of the present disclosure are shown schematically. In method 240, a structure 250 is shown having a substrate 248 with a device layer 243 or compliant layer disposed on top of the substrate. Structure 250 shows a partial cut 254 into the substrate. FIG. 2B shows a cross-sectional view 252 of structure 250.

In certain aspects, as shown in FIG. 2B, a portion of the substrate is removed using an etchant such as an acid. Structure 262 shows the structure after the substrate is partially removed. Structure 272 shows the break-away of excess substrate. In certain aspects, the disclosure provides a structure 250, 262 and 272.

In certain aspects, the disclosure provides a substrate having a cantilever device or complaint layer disposed on top thereof.

Figure 3A:
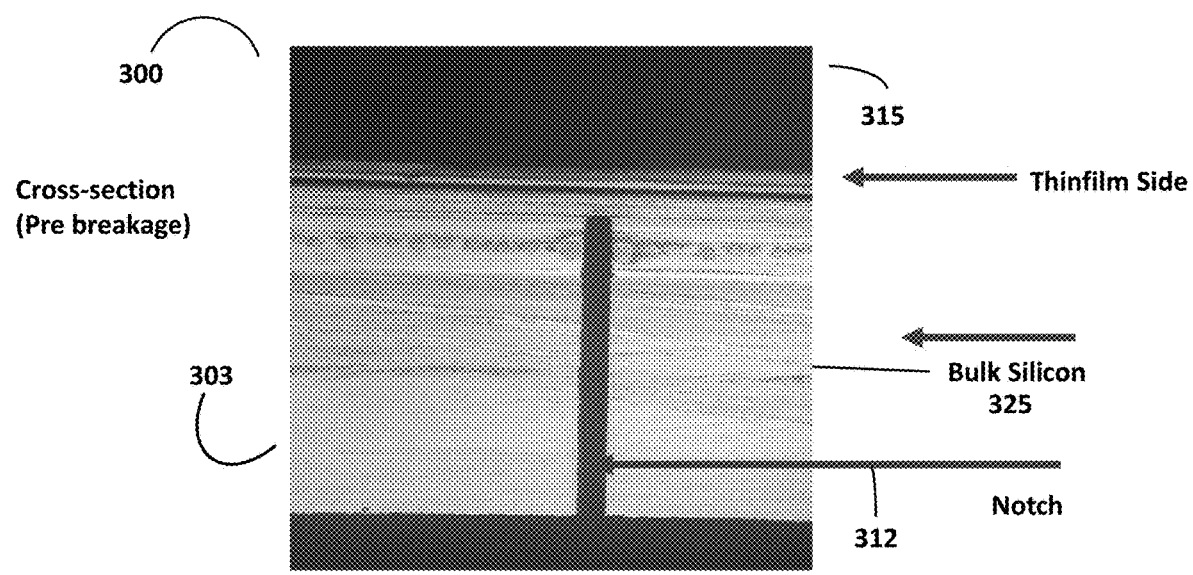
FIG. 3A shows a cross-sectional view of a substrate of the present disclosure.

FIG. 3A shows an exemplary cross-sectional view of a substrate 300 of the present disclosure. A partial cut or notch 312 is shown in a silicon wafer 303. In this method, a wafer singulation is made by using a partial-saw and break method. A saw cut creates a notch or fault line so that the right-side 325 of the wafer can be separated from the left-side of the wafer.

The singulation step is a characteristic part of the fabrication of the cantilever. The die portions must be separated from each other in such a manner so as not to damage the chip components. Singulation is performed in a sawing and breaking process that is designed to ensure device integrity to the greatest extent possible. In certain aspects, the substrate singulation methods of the present disclosure provides a partial-saw and break method. A saw cut creates a fault-line so that the substrate can be separated into two pieces using for example, an impact tool.

Partially sawing through a substrate (e.g., silicon wafer) to create a notch or fault-line, and thereafter impacting the partially sawed region with an impact tool generates a relatively clean break. In certain aspects, the partial cuts, notches or fault-lines are made using a saw blade having a width of about 50 microns to about 254 microns (10 mils) and produce a cut approximately 85% to about 99% of through the substrate. In addition to a partial cut, a full-cut through the substrate (100%) can also be done. A full cut can also be performed using a 10 mil saw blade or smaller.

Figure 3B:
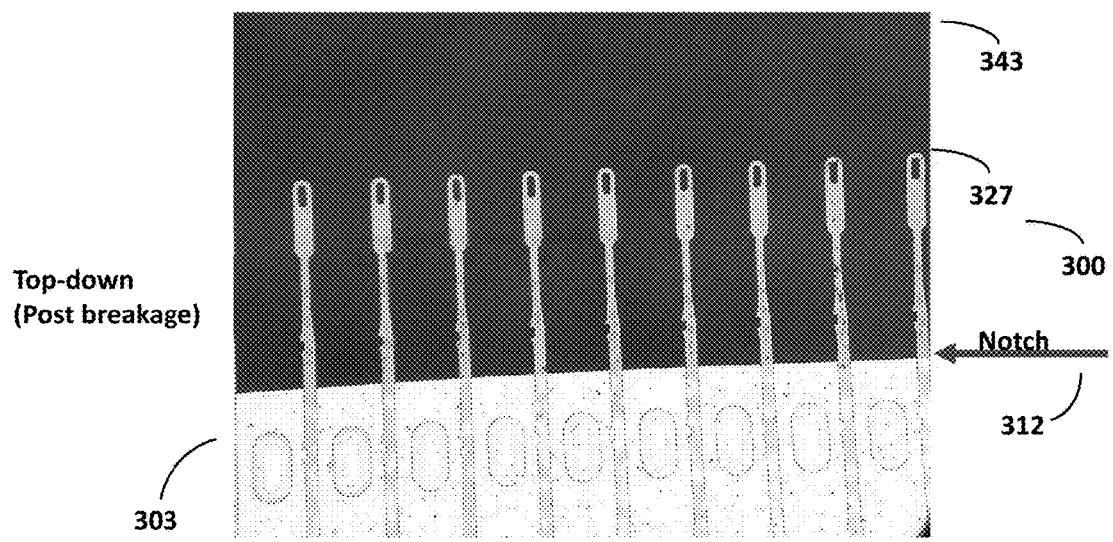
FIG. 3B shows an exemplary top-down view of a substrate of the present disclosure.

FIG. 3B shows an exemplary top-down view of a substrate 300 of the present disclosure after the fault-line is broken. FIG. 3B represents a substrate following method 100. Following a break of the notch or fault-line 312, a free space 343 is formed, wherein a device such as an implantable electrode 327 is exposed to allow a robot to implant. Implantation can be into the brain of a mammal. In certain aspects, free space is beneath the electrodes.

Figure 4:
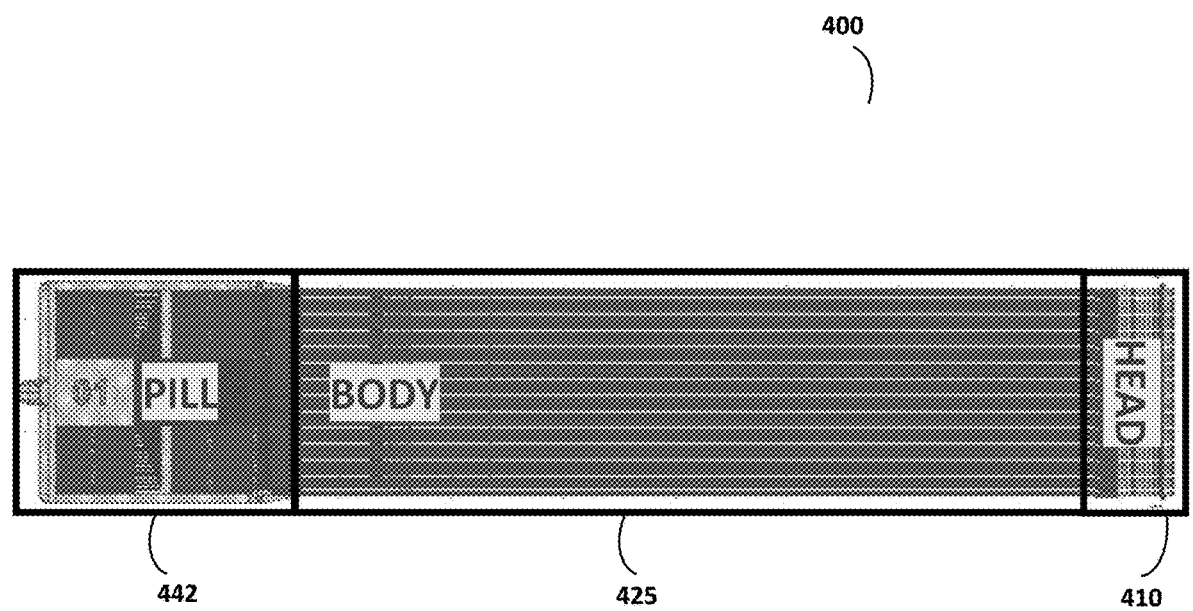
FIG. 4 shows an exemplary top-down view of a substrate of the present disclosure.

FIG. 4 shows an exemplary top-down view of a substrate 400 of the present disclosure. As shown, there are at least three (3) segments of the substrate. A head section 410, a body section 425 and a pill section 442. The head section 410 is useful for thread management and/or or facilitating implantation. The body section 425 is useful for a peel force measurement and the pill section 442 is useful for electrochemical testing. The head area 410 can hold an array of threads or neural electrodes for implantation.

Figure 5:
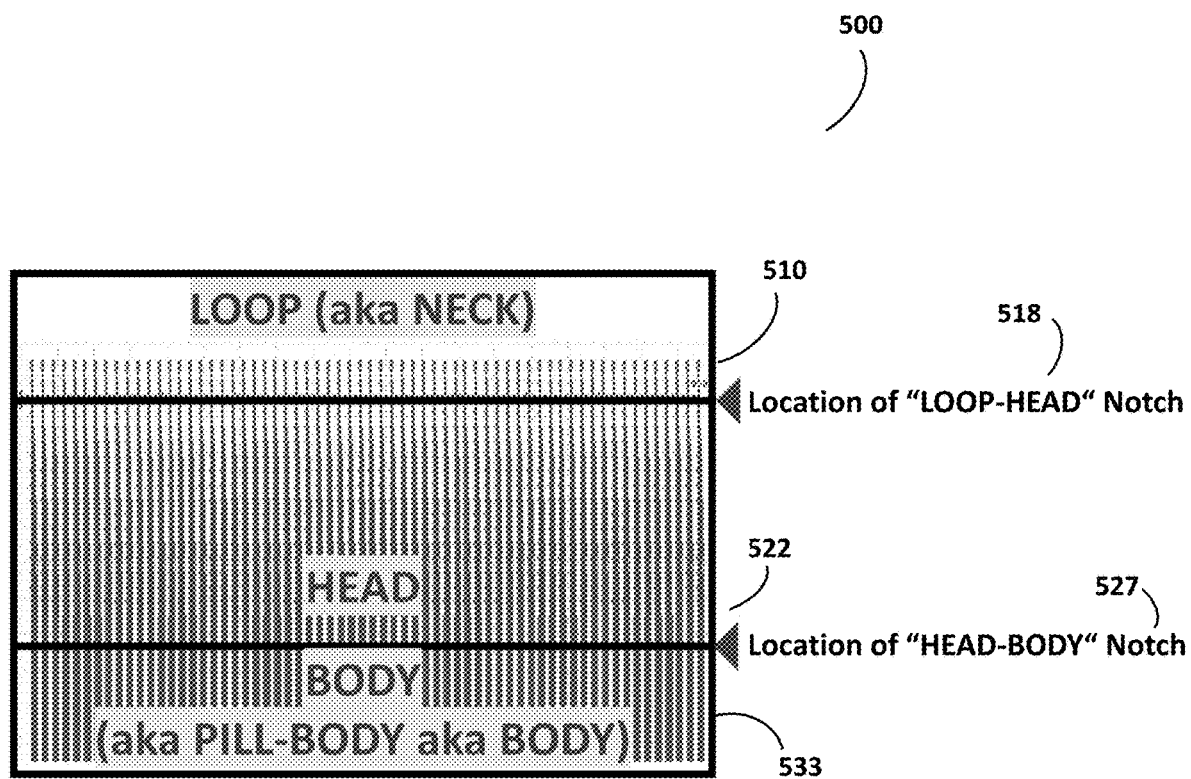
FIG. 5 shows an exemplary top-down view of a substrate of the present disclosure.

FIG. 5 shows an exemplary top-down view of a substrate 500 of the present disclosure. As shown, there are at least three (3) segments of the substrate. A loop section 510 containing the loop of a thread. A head section 522 and a body section 533. There are at least two (2) notches or fault lines 518 and 527. Fault line 518 is between the loop section 510 and the head section 522. Fault line 512 is between head section 522 and body section 533.

Advantageously, the threads at the interface of the notch or fault line are not bent during breaking. An aluminum release layer is maintained and in certain aspects, the order of operations is: (i) dice singulate arrays; (ii) etch aluminum; and (iii) 'Snap' or break the neck. With this order of operation, when silicon is broken, the device (PI) is not on silicon but instead 'floating', due to aluminum underneath already being etched away.

In certain aspects, the sacrificial layer is removed using an etchant. Etchants include dilute HF, buffered HF, nitric acid, etc.

In certain aspects, the compliant layer comprises a device. The device can be an implantable device into a mammal such as a human.

In certain aspects, the compliant layer is made or fabricated from a material, which is a member selected from polyimide, parylene C, SU-8 photoresist or benzocyclobutene (BCB).

In certain aspects, the compliant layer is a device comprising polyimide. The device can be implantable device such as one or more neural electrodes.

In certain aspects, breaking the substrate along the at least one linear partial cut to generate a cantilever section can be performed in a solution or in air.

In certain aspects, breaking step is done manually or in automated fashion.

In certain aspects, the disclosure provides a structure made by the present methods.

In certain, a wafer saw is used to make partial cut(s) on the backside that is opposite to the frontside where the overhang structure is released. This is done so to minimize detrimental effects related to dicing, e.g. inadvertent damage to the overhang structure and incorporation of particles/contaminants. Conventional use of through-cuts is made on the same side of the substrate to singulate the device.

Following dicing, die-level processing (such as solvent cleans) ensues, and the overhang structure is released from a sacrificial layer or substrate using an etchant. Either a wet or dry etchant can be used. The preference to release the overhang structure only after partial cut(s) comes from the desire to minimize inadvertent damage to the overhang structure and incorporation of particles/contaminants.

Following release, a breakaway operation is performed to remove the substrate material immediately underneath the overhang structure. This operation could be performed with the overhang structure in a solution (i.e., wet) or in air (i.e., dry). The breakaway operation can be performed manually (e.g., using tweezers) or in an automated fashion (e.g. impulse bar and fixturing).

This sequence of operation minimizes inadvertent damage due to capillary effects to the overhang structure during drying.

While it is possible to make the partial cut(s) into the sacrificial layer and avoid the post-release break altogether, this is increasingly difficult with thinner sacrificial layers. Additionally, the residual substrate material from the partial cut(s) can be removed using etchant(s) to avoid a post-release break as well.

In another embodiment, the present disclosure provides a process of forming a plurality of active areas on the surface of a wafer to make a plurality of dice. The method provides singulating a substrate such as a silicon wafer assembly having a substrate populated with a plurality of dice, the method comprising:
  forming a linear partial cut into the substrate;
  cutting through the substrate along at least one line substantially perpendicular to the linear partial cut; and
  cutting through the substrate along at least one line substantially parallel to the linear partial cut.

Figure 6:
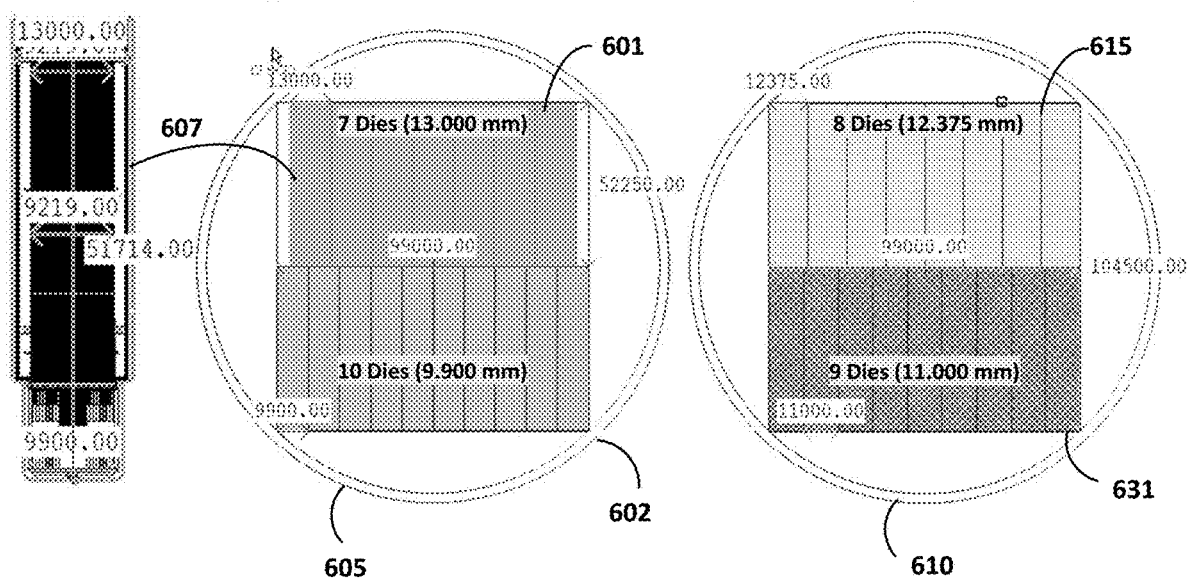
FIG. 6 shows a wafer map of the present disclosure.

FIG. 6 shows an exemplary top-down view of a substrate wafer map of the present disclosure. Wafer map 605 shows 7 dice such as 601 wherein each of the 7 die is 13 mm in width or X direction. Enlarged die 607 shows the die in more detail.

Wafer map 605 shows a die 602 that has dice that are 9.900 mm in the X direction. Wafer map 610 shows 8 dice, wherein 5615 is exemplary with a X direction length of 15.375 mm. Wafer map 610 has a die 631 which is 11.000 mm in the X direction.

Modifications and variations of the present invention will be obvious to those skilled in the art from the foregoing detailed description and are intended to fall within the scope of the following claims. The teachings of all references cited herein are specifically incorporated by reference.

What is claimed is:

1. A method for fabricating a cantilever section in a structure, the method comprising:
   obtaining the structure comprising a substrate and a compliant layer or comprising the substrate, the compliant layer, and a sacrificial layer therebetween, the compliant layer being made or fabricated from a material which is at least one selected from the group consisting of polyimide, parylene C, SU-8 photoresist, and benzocyclobutene (BCB);
   cutting part-way through the substrate to create an at least one linear partial cut;
   undercutting into the substrate or undercutting into the substrate and releasing the sacrificial layer from the structure; and
   breaking the substrate along the at least one linear partial cut to generate the cantilever section in the substrate.

2. The method according to claim 1, wherein the substrate is at least one selected from the group consisting of a wafer, a plate, and a film.

3. The method according to claim 1, wherein the substrate comprises silicon.

4. The method according to claim 1, wherein the substrate is a silicon wafer.

5. The method according to claim 1, wherein the compliant layer comprises a device.

6. The method according to claim 1, wherein the compliant layer is made or fabricated from the material which is at least one selected from the group consisting of polyimide, SU-8 photoresist, and benzocyclobutene (BCB).

7. The method according to claim 1, wherein the compliant layer comprises a device comprising polyimide.

8. The method according to claim 7, wherein the device is implantable.

9. The method according to claim 5, wherein the device is configured as a neural electrode.

10. The method according to claim 1, wherein the structure comprises the substrate, the compliant layer, and the sacrificial layer therebetween.

11. The method according to claim 10, wherein the sacrificial layer is made or fabricated from a material which is at least one selected from the group consisting of aluminum, chromium, silicon oxide, titanium, and tungsten.

12. The method according to claim 11, wherein the releasing of the sacrificial layer from the structure includes etching.

13. The method according to claim 1, wherein the breaking of the substrate along the linear partial cut to generate the cantilever section is performed in a solution or in air.

14. The method according to claim 1, wherein the linear partial cut is formed on a surface of the substrate opposite the compliant layer.

15. The method according to claim 1, wherein the linear partial cut is formed through 85% to 99% of a thickness of the substrate.

16. The method according to claim 1, wherein the cantilever section is coplanar with a section of the compliant layer on the substrate.

17. The method according to claim 1, wherein the undercutting includes etching.

18. The method according to claim 1, wherein the linear partial cut has a width of about 50 microns to about 254 microns.

19. A structure made by the method of claim 1.

20. A method for fabricating a cantilever section in a structure, the method comprising:
- obtaining the structure comprising a substrate and a compliant layer or comprising the substrate, the compliant layer, and a sacrificial layer therebetween, the compliant layer comprising a device comprising polyimide;
- cutting part-way through the substrate to create an at least one linear partial cut;
- undercutting into the substrate or undercutting into the substrate and releasing the sacrificial layer from the structure; and
- breaking the substrate along the at least one linear partial cut to generate the cantilever section in the substrate.

* * * * *